(12) United States Patent
Lee et al.

(10) Patent No.: US 9,487,460 B2
(45) Date of Patent: Nov. 8, 2016

(54) METHOD FOR PRODUCING ALLYL ALCOHOL AND ALLYL ALCOHOL PRODUCED THEREBY

(71) Applicant: LG CHEM, LTD., Seoul (KR)

(72) Inventors: Won Jae Lee, Daejeon (KR); Myungjin Kong, Daejeon (KR); Yong-Jin Choe, Daejeon (KR); Hyun Nam, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/893,304

(22) PCT Filed: Jun. 27, 2014

(86) PCT No.: PCT/KR2014/005760
§ 371 (c)(1),
(2) Date: Nov. 23, 2015

(87) PCT Pub. No.: WO2014/209068
PCT Pub. Date: Dec. 31, 2014

(65) Prior Publication Data
US 2016/0115109 A1 Apr. 28, 2016

(30) Foreign Application Priority Data

Jun. 27, 2013 (KR) .................. 10-2013-0074507
Jun. 26, 2014 (KR) .................. 10-2014-0078769

(51) Int. Cl.
*C07C 33/03* (2006.01)
*C07C 29/60* (2006.01)

(52) U.S. Cl.
CPC .............. *C07C 29/60* (2013.01); *C07C 33/03* (2013.01)

(58) Field of Classification Search
CPC ...................................... C07C 33/03
USPC ............................. 568/909.5, 852
See application file for complete search history.

(56) References Cited

U.S. PATENT DOCUMENTS

| | | | |
|---|---|---|---|
| 4,072,727 A | 2/1978 | Vanderspurt | |
| 5,892,066 A | 4/1999 | Grey | |
| 7,396,962 B1 | 7/2008 | Dubois et al. | |
| 7,655,818 B2 | 2/2010 | Dubois et al. | |
| 7,683,220 B2 | 3/2010 | Matsunami et al. | |
| 7,718,829 B2 | 5/2010 | Masaaki et al. | |
| 7,951,978 B2 | 5/2011 | Arita et al. | |
| 8,273,926 B2 | 9/2012 | Bergman et al. | |
| 2009/0287004 A1* | 11/2009 | Bergman ................ | C07C 29/60 549/508 |

FOREIGN PATENT DOCUMENTS

| | | |
|---|---|---|
| JP | 2004-339196 A | 12/2004 |
| JP | 2012-232903 A | 11/2012 |
| JP | 5095203 B2 | 12/2012 |
| KR | 10-2013-0043606 A | 4/2013 |
| WO | 2008/092115 A1 | 7/2008 |
| WO | 2011/108509 A1 | 9/2011 |

OTHER PUBLICATIONS

Jing Yi et al.: "Rhenium-Catalyzed Transfer Hydrogenation and Deoxygenation of Biomass-Derived Polyols to Small and Useful Organics", CHEMSUSCHEM, 2012, vol. 5, pp. 1401-1404.

Mika Shiramizu et al.: "Deoxygenation of Biomass-Derived Feedstocks: Oxorhenium-Catalyzed Deoxydehydration of Sugars and Sugar Alcohols", Angewandte. Chem. Int. Ed., 2012, vol. 51, pp. 8082-8086.

Oliver Kamm et al.: "Allyl Alcohol", Organic Syntheses, vol. 1, pp. 1941-1942.

Elena Arceo et al.: "An efficient didehydroxylation method for the biomass-derived polyols glycerol and erythritol. Mechanistic studies of a formic acid-mediated deoxygenation", ChemComm, 2009, pp. 3357-3359.

* cited by examiner

*Primary Examiner* — Elvis O Price

(74) *Attorney, Agent, or Firm* — Dentons US LLp

(57) ABSTRACT

Disclosed are a method of preparing allyl alcohol and allyl alcohol prepared thereby. The method of preparing allyl alcohol includes adding glycerol with formic acid in an amount of 0.8~2 equivalents relative to 1 equivalent of glycerol, and increasing a reaction temperature to 220~260° C. from room temperature at a heating rate of 2.0~7.0° C./min so that glycerol and formic acid are reacted.

8 Claims, No Drawings

METHOD FOR PRODUCING ALLYL ALCOHOL AND ALLYL ALCOHOL PRODUCED THEREBY

This application is a National Stage Entry of International Application No. PCT/KR2014/005760, filed Jun. 27, 2014, and claims the benefit of and priority to Korean Application Nos. 10-2013-0074507, filed on Jun. 27, 2013 and 10-2014-0078769, filed on Jun. 26, 2014, all of which are hereby incorporated by reference in their entirety for all purposes as if fully set forth herein.

TECHNICAL FIELD

The present invention relates to a method of preparing allyl alcohol from glycerol and allyl alcohol prepared thereby. More particularly, the present invention relates to a method of preparing allyl alcohol from glycerol using formic acid in a specific equivalent amount at a specific reaction temperature, and to allyl alcohol prepared thereby.

BACKGROUND ART

Allyl alcohol has been mainly utilized to prepare polymer resins, medical products and fine chemical products, and is mostly derived from propylene obtained by petrochemical processes.

To overcome problems of fossil fuel exhaustion, techniques for synthesizing biodiesel from biomass, for example, vegetable or animal oil, have been commercialized, and the demand therefor is increasing.

Typically, biodiesel is produced via transesterification of vegetable oil and alcohol. In this procedure, glycerol is produced as a byproduct. This glycerol may be employed in a large amount, and is a renewable material that may be easily stored or transported, and is thus regarded as a promising material for preparation of allyl alcohol.

Preparation of allyl alcohol from glycerol is based on a two-step reaction mechanism, including a first step for dehydration of glycerol into acrolein and a second step for hydrogenation of acrolein into allyl alcohol.

In this regard, the first step is disclosed in U.S. Pat. Nos. 7,396,962, 7,655,818, 7,683,220, 7,718,829, and 7,951,978, and the second step is disclosed in U.S. Pat. Nos. 4,072,727, and 5,892,066. However, these reaction processes are complicated and difficult to carry out, and result in high separation and purification costs, and thus become unsuitable for use in industrial mass production. Moreover, such processes, which are carried out in the presence of a catalyst, are problematic because the catalyst has to be periodically replaced and high costs may result.

Direct preparation of allyl alcohol from glycerol not through acrolein is described in ChemSusChem 2012, Vol 5, pp 1401-1404, but employs a catalyst, undesirably generating byproducts such as 1,3-dihydroxyacetone. Also, as disclosed in Angew. Chem. Int. Ed. 2012, Vol 51, pp 8082-8086, the preparation process requires the use of an expensive rhenium catalyst, and is thus inappropriate for use in industrial mass production.

Although preparation of allyl alcohol from glycerol without the use of a catalyst was proposed (Kamm et al, Organic Syntheses, Coll. Vol. 1, 1941), the allyl alcohol yield was very low.

Therefore, with the goal of preparing allyl alcohol from glycerol, a byproduct of a biodiesel synthesis process, there is an urgent need for a method of preparing allyl alcohol at high yield via liquid reaction at relatively low reaction temperature without the use of a catalyst.

DISCLOSURE

Technical Problem

The present invention has been made keeping in mind the above problems encountered in the related art, and an object of the present invention is to provide a method of preparing allyl alcohol at high yield from glycerol via liquid reaction at relatively low reaction temperature without the use of a catalyst.

Technical Solution

In order to accomplish the above object, the present invention provides a method of preparing allyl alcohol, comprising mixing glycerol with formic acid in an amount of 0.8~2 equivalents relative to 1 equivalent of glycerol, and reacting them at a reaction temperature of 220~260° C.

In addition, the present invention provides allyl alcohol prepared by the method as described above.

Advantageous Effects

According to the present invention, a method of preparing allyl alcohol enables the allyl alcohol to be produced at a high yield of 80% or more via liquid reaction at relatively low reaction temperature without the use of a catalyst.

BEST MODE

Hereinafter, a detailed description will be given of a method of preparing allyl alcohol according to the present invention.

The present invention addresses a method of preparing allyl alcohol, comprising mixing glycerol with formic acid in an amount of 0.8~2 equivalents relative to 1 equivalent of glycerol, and increasing a reaction temperature to 220~260° C. from room temperature at a heating rate of 2.0~7.0° C./min so that glycerol and formic acid are reacted.

Glycerol is a compound represented by $HOCH_2(CHOH)CH_2OH$, and is also referred to as trihydroxypropane or glycerin. Although the purity of glycerol does not limit the scope of the present invention, it is 80 wt % or higher, preferably 90 wt % or higher, and more preferably 95 wt % or higher, in order to reduce production of reaction byproducts.

In the present invention, the inventors utilized the glycerol which can be obtained as a byproduct from a biodiesel synthesis process via transesterification of vegetable oil and alcohol.

The method of preparing allyl alcohol from glycerol according to the present invention is a liquid phase reaction, which is carried out at a relatively low temperature, namely, 300° C. or less, compared to a gas phase reaction. Hence, this reaction is favorable in terms of energy costs, compared to conventional preparation of allyl alcohol via gas reaction.

Direct preparation of allyl alcohol via reaction between glycerol and formic acid according to the present invention is conducted as in Scheme 1 below.

[Scheme 1]

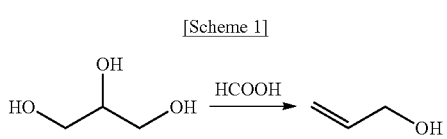

In Scheme 1, carboxylic acid reacting with glycerol is exemplified by formic acid. As such, formic acid is advantageous because carbon dioxide, which is produced as a reaction byproduct of allyl alcohol preparation, may thus be easily removed. The other carboxylic acids may generate byproducts, and undesirably require additional separation and purification processes.

When the method of preparing allyl alcohol according to the present invention is performed in an oxygen-containing gas atmosphere, oxidative decomposition of glycerol or carbonization may occur, which may result in lowering the product yield. Hence, this reaction is preferably carried out in an inert gas atmosphere.

The inert gas may be any one selected from the group consisting of nitrogen, argon and helium, and the gas phase reaction products may include at least one selected from the group consisting of carbon dioxide, water vapor, allyl formate, allyl alcohol, and unreacted formic acid. The liquid phase reaction products may include at least one selected from the group consisting of allyl alcohol, allyl formate, unreacted formic acid, and water.

As shown in Scheme 1, since glycerol and formic acid react at 1:1, the equivalent amount herein refers to a molar amount.

In the method of preparing allyl alcohol according to the present invention, the reaction temperature is increased to 220~260° C., preferably 230~250° C., and more preferably 230~240° C., thus enabling the production of allyl alcohol at high yield from glycerol. If the reaction temperature is lower than 220° C., the reaction intermediate, glyceryl formate, does not proceed to the next step. In contrast, if the reaction temperature is higher than 260° C., the reaction byproduct, allyl formate, may be produced in a significant amount.

In the method of preparing allyl alcohol according to the present invention, the heating rate may be set to 2.0~7.0° C./min so that the reaction temperature for reacting glycerol and formic acid reaches 220~260° C. from room temperature. If the heating rate is less than 2.0° C./min, the production of allyl formate may increase. In contrast, if the heating rate is higher than 7.0° C./min, the rate of vaporization of formic acid may drastically increase, undesirably resulting in the remarkable decrease of the glycerol conversion.

In the method of preparing allyl alcohol according to the present invention, formic acid is used in an amount of 0.8~2 equivalents, and preferably 1.2~1.7 equivalents, relative to 1 equivalent of glycerol. If the amount of formic acid is less than the lower limit, the allyl alcohol selectivity may increase whereas the glycerol conversion may decrease, undesirably resulting in low allyl alcohol yield. In contrast, if the amount of formic acid exceeds the upper limit, the glycerol conversion may increase but the allyl alcohol selectivity may decrease, undesirably lowering the allyl alcohol yield.

In the method of preparing allyl alcohol according to the present invention, the allyl alcohol is prepared at a yield of 60% or more, and preferably 75% or more.

Since the allyl alcohol yield prepared by the method as above is high, it may be industrially useful.

Also, since a catalyst as disclosed in ChemSusChem 2012, Vol 5, pp 1401-1404 is not used in the present invention, byproducts such as 1,3-dihydroxyacetone are not generated. Furthermore, the reaction of the present invention proceeds without using an expensive rhenium catalyst as disclosed in Angew. Chem. Int. Ed. 2012, Vol 51, pp 8082-8086, and is thus economically suitable for industrial mass production.

The method of the present invention may be performed using any one or more selected from among a batch reactor, a continuous stirred tank reactor (CSTR), and a plug flow reactor (PFR), which are typically used by those skilled in the art, and the kind and combination thereof are not limited herein.

MODE FOR INVENTION

The following examples of the present invention are disclosed for illustrative purposes, but those skilled in the art will appreciate that various modifications, additions and substitutions are possible, without departing from the scope and spirit of the invention as disclosed in the accompanying claims.

EXAMPLE

Example 1

In a flask reactor (F1) in a helium atmosphere, 27.6 g (300 mmol) of glycerol and 20.71 g (450 mmol) of formic acid were placed such that formic acid was added in an amount of 1.5 equivalents relative to 1 equivalent of glycerol, and the temperature of the reaction mixture was increased to 230° C. at a rate of 4.2° C./min with slow stirring and then maintained for 2.5 hr, yielding allyl alcohol.

Example 2

Allyl alcohol was prepared in the same manner as in Example 1, with the exception that the reaction temperature was 240° C.

Example 3

Allyl alcohol was prepared in the same manner as in Example 1, with the exception that the reaction temperature was 250° C.

Example 4

In a flask reactor (F1) in a helium atmosphere, 27.6 g (300 mmol) of glycerol and 13.8 g (300 mmol) of formic acid were placed such that formic acid was added in an amount of 1.0 equivalent relative to 1 equivalent of glycerol, and the temperature of the reaction mixture was increased to 230° C. with slow stirring and then maintained for 2.5 hr, yielding allyl alcohol.

Example 5

Allyl alcohol was prepared in the same manner as in Example 4, with the exception that formic acid was added in an amount of 2.0 equivalents.

Example 6

Allyl alcohol was prepared in the same manner as in Example 4, with the exception that formic acid was added in an amount of 0.8 equivalents.

Example 7

Allyl alcohol was prepared in the same manner as in Example 4, with the exception that formic acid was added in an amount of 1.2 equivalents.

Example 8

Allyl alcohol was prepared in the same manner as in Example 4, with the exception that formic acid was added in an amount of 1.7 equivalents.

Comparative Example 1

Allyl alcohol was prepared in the same manner as in Example 1, with the exception that the reaction temperature was 200° C.

Comparative Example 2

Allyl alcohol was prepared in the same manner as in Example 1, with the exception that the heating rate was 1.5° C./min.

Comparative Example 3

Allyl alcohol was prepared in the same manner as in Example 4, with the exception that formic acid was added in an amount of 0.60 equivalents.

Comparative Example 4

Allyl alcohol was prepared in the same manner as in Example 4, with the exception that formic acid was added in an amount of 3.0 equivalents.

In the allyl alcohol preparation processes of Examples 1 to 8 and Comparative Examples 1 to 4, the formic acid equivalent and the reaction temperature are summarized in Table 1 below.

TABLE 1

|  | Formic acid equiv. (relative to 1 equiv. of glycerol) | Reaction temp. (° C.) | Heating rate (° C./min) |
| --- | --- | --- | --- |
| Ex. 1 | 1.5 | 230 | 4.2 |
| Ex. 2 | 1.5 | 240 | 4.2 |
| Ex. 3 | 1.5 | 250 | 4.2 |
| Ex. 4 | 1.0 | 230 | 4.2 |
| Ex. 5 | 2.0 | 230 | 4.2 |
| Ex. 6 | 0.8 | 230 | 4.2 |
| Ex. 7 | 1.2 | 230 | 4.2 |
| Ex. 8 | 1.7 | 230 | 4.2 |
| C. Ex. 1 | 1.5 | 200 | 4.2 |
| C. Ex. 2 | 1.5 | 230 | 1.5 |
| C. Ex. 3 | 0.6 | 230 | 4.2 |
| C. Ex. 4 | 3.0 | 230 | 4.2 |

TEST EXAMPLE

The allyl alcohol and unreacted glycerol concentrations in the above examples and comparative examples were analyzed using gas chromatography (GC 6890N, Agilent). To this end, as the reactions described in Examples 1 to 8 and Comparative Examples 1 to 4 progressed, unreacted formic acid, water and allyl alcohol, which are vaporized from the liquid mixture, were passed through a condenser connected to the reactor (F1) and then the condensates were collected in a flask (F2) placed at the end of the condenser. To calculate the yield, after termination of the reaction, 8.29 g (60 mmol) of calcium carbonate was added in the flask (F2) so as for neutralization and salting out, and the organic layer was extracted, and the allyl alcohol yield was calculated. Also, to calculate the glycerol conversion and allyl alcohol selectivity, the sample collected in the flask (F2) placed at the end of the condenser was quantitatively analyzed using gas chromatography (GC 6890N, Agilent). After termination of the reaction for 2.5 hr, the reactor (F1) was cooled, and unreacted glycerol was quantitatively analyzed using gas chromatography (GC 6890N, Agilent). As such, allyl alcohol was absent in the reactor (F1), but formic acid was present in the reactor (F1) and the flask (F2) provided to the end of the condenser.

Based on the measurement results as above, the glycerol conversion, allyl alcohol selectivity, and allyl alcohol yield were calculated using Equations 1 to 3 below. The results are shown in Table 2 below.

$$\text{Glycerol conversion (\%)} = 100 \times \frac{\text{mol of reacted glycerol}}{\text{mol of glycerol before reaction}} \quad [\text{Equation 1}]$$

$$\text{Allyl alcohol selectivity (\%)} = 100 \times \frac{\text{mol of produced allyl alcohol}}{\text{mol of reacted glycerol}} \quad [\text{Equation 2}]$$

$$\text{Allyl alcohol yield (\%)} = \frac{\text{Glycerol conversion} \times \text{Allyl alcohol selectivity}}{100} \quad [\text{Equation 3}]$$

Test Example 1

Effect of Temperature on Glycerol Conversion, Allyl Alcohol Selectivity, and Allyl Alcohol Yield Effect of temperature on the glycerol conversion, allyl alcohol selectivity, and allyl alcohol yield is shown in Table 2 below.

TABLE 2

|  | Reaction temp. (° C.) | Glycerol conversion (%) | Allyl alcohol selectivity (%) | Allyl alcohol yield (%) |
| --- | --- | --- | --- | --- |
| Ex. 1 | 230 | 95 | 85 | 80.7 |
| Ex. 2 | 240 | 96 | 74 | 71.0 |
| Ex. 3 | 250 | 92 | 71 | 65.3 |
| C. Ex. 1 | 200 | 92 | 2 | 1.8 |

As shown in Table 2, in Examples 1 to 3 and Comparative Example 1 where different reaction temperatures were used while the same amount of formic acid was added, the maximum allyl alcohol yield was obtained at 230° C. As the reaction temperature increased to 250° C., the allyl alcohol selectivity decreased, resulting in lowering allyl alcohol yield. On the other hand, the allyl alcohol yield of Comparative Example 1 was very low at a reaction temperature of 200° C.

Test Example 2

Effect of Formic Acid Equivalent on Glycerol Conversion, Allyl Alcohol Selectivity, and Allyl Alcohol Yield Effect of formic acid equivalent on the glycerol conversion, allyl alcohol selectivity, and allyl alcohol yield is shown in Table 3 below.

TABLE 3

|  | Formic acid equiv. | Glycerol conversion (%) | Allyl alcohol selectivity (%) | Allyl alcohol yield (%) |
| --- | --- | --- | --- | --- |
| Ex. 1 | 1.5 | 95 | 85 | 80.7 |
| Ex. 4 | 1.0 | 84 | 84 | 70.6 |
| Ex. 5 | 2.0 | 99 | 68 | 67.3 |
| Ex. 6 | 0.8 | 72 | 89 | 64.1 |
| Ex. 7 | 1.2 | 90 | 84 | 75.6 |
| Ex. 8 | 1.7 | 97 | 78 | 75.7 |
| C. Ex. 3 | 0.6 | 50 | 92 | 46.0 |
| C. Ex. 4 | 3.0 | 97 | 38 | 36.8 |

As shown in Table 3, in Examples 1, 4 to 8 and Comparative Examples 3 and 4 where different formic acid equivalents were added while the same reaction temperature were used, the maximum allyl alcohol yield was obtained at an amount of 1.50 equivalents. In Comparative Example 3 using formic acid in an amount of 0.60 equivalents, the allyl alcohol selectivity was high but the glycerol conversion was low, and thus the allyl alcohol yield was only 46%. When formic acid was used in an amount of 3.00 equivalents, the allyl alcohol selectivity was decreased and thus the allyl alcohol yield was lowered. Also, when formic acid was used in an amount of 0.8~2 equivalents, the allyl alcohol yield was 60% or more, and when formic acid was used in an amount of 1.2~1.7 equivalents, the allyl alcohol yield reached maximum of 75% or higher.

Test Example 3

Effect of Heating Rate on Glycerol Conversion, Allyl Alcohol Selectivity, and Allyl Alcohol Yield Effect of heating rate on the glycerol conversion, allyl alcohol selectivity, and allyl alcohol yield is shown in Table 4 below.

TABLE 4

|  | Heating rate (° C./min) | Glycerol conversion (%) | Allyl alcohol selectivity (%) | Allyl alcohol yield (%) |
| --- | --- | --- | --- | --- |
| Ex. 1 | 4.2 | 95 | 85 | 80.7 |
| C. Ex. 2 | 1.5 | 89 | 61 | 54.2 |

As shown in Table 4, in Example 1 and Comparative Example 2 where different heating rates were applied while the same reaction temperature were used and the same amount of formic acid was added, both the conversion and the selectivity were decreased as the heating rate was lower.

Based on the analytical results of Tables 2 through 4, the allyl alcohol yield can be remarkably increased within the certain range of the reaction temperature, heating rate and formic acid equivalent in the method of preparing allyl alcohol according to the present invention, thereby exhibiting superior effects.

The invention claimed is:

1. A method of preparing allyl alcohol, comprising mixing glycerol with formic acid in an amount of 0.8~2 equivalents relative to 1 equivalent of glycerol, and increasing a reaction temperature to 220~260° C. from room temperature at a heating rate of 2.0 ~7.0° C./min so that glycerol and formic acid are reacted.

2. The method of claim 1, wherein formic acid is added in an amount of 1.2~1.7 equivalents.

3. The method of claim 1, wherein the heating rate is 4.0~7.0° C./min.

4. The method of claim 1, wherein the reaction temperature is 230~250° C.

5. The method of claim 1, wherein glycerol and formic acid are reacted in an inert gas atmosphere.

6. The method of claim 5, wherein the inert gas is helium, nitrogen or argon.

7. The method of claim 1, wherein an allyl alcohol yield is 60% or more.

8. The method of claim 1, wherein an allyl alcohol yield is 75% or more.

* * * * *